United States Patent
Bossy et al.

(10) Patent No.: US 10,493,155 B2
(45) Date of Patent: Dec. 3, 2019

(54) HEAT-STERILIZED FORMULATION COMPRISING CHITOSAN AND PROCESS OF PREPARATION THEREOF

(71) Applicant: LABORATOIRE MEDIDOM SA, Sarnen (CH)

(72) Inventors: Leila Yolanda Bossy, Gingins (CH); Alessandro Di Napoli, Collonge-Bellerive (CH)

(73) Assignee: LABORATOIRE MEDIDOM SA, Sarnen (CH)

( * ) Notice: Subject to any disclaimer, the term of this patent is extended or adjusted under 35 U.S.C. 154(b) by 85 days.

(21) Appl. No.: 15/522,789

(22) PCT Filed: Oct. 28, 2015

(86) PCT No.: PCT/IB2015/058300
§ 371 (c)(1),
(2) Date: Apr. 28, 2017

(87) PCT Pub. No.: WO2016/067210
PCT Pub. Date: May 6, 2016

(65) Prior Publication Data
US 2017/0312364 A1 Nov. 2, 2017

(30) Foreign Application Priority Data

Oct. 29, 2014 (EP) .................. PCT/EP2014/073246

(51) Int. Cl.
| | |
|---|---|
| *A61K 47/10* | (2017.01) |
| *A61K 47/12* | (2006.01) |
| *A61K 47/36* | (2006.01) |
| *C08L 5/08* | (2006.01) |
| *A61L 2/00* | (2006.01) |
| *C08L 5/00* | (2006.01) |
| *A61K 9/00* | (2006.01) |
| *A61K 9/08* | (2006.01) |
| *A61K 31/722* | (2006.01) |

(52) U.S. Cl.
CPC ............ *A61K 47/12* (2013.01); *A61K 9/0019* (2013.01); *A61K 9/0048* (2013.01); *A61K 9/08* (2013.01); *A61K 31/722* (2013.01); *A61K 47/10* (2013.01); *A61K 47/36* (2013.01); *A61L 2/0023* (2013.01); *C08L 5/00* (2013.01); *C08L 5/08* (2013.01); *A61L 2202/21* (2013.01); *C08L 2201/54* (2013.01); *C08L 2203/02* (2013.01); *C08L 2205/02* (2013.01)

(58) Field of Classification Search
CPC ...... A61K 31/722; A61K 47/10; A61K 47/12; A61K 47/36; A61K 9/08; A61K 9/0019; A61K 9/0048; A61L 2201/21; A61L 2/0023; C08L 2205/02; C08L 2203/02; C08L 2201/54; C08L 5/08; C08L 5/00
USPC ......................................................... 514/55
See application file for complete search history.

(56) References Cited

U.S. PATENT DOCUMENTS

| 4,659,700 A | 4/1987 | Jackson |
| 2002/0119949 A1 | 8/2002 | Hellman et al. |
| 2009/0142292 A1* | 6/2009 | Blackwell ............... G02B 1/043 424/78.04 |

FOREIGN PATENT DOCUMENTS

| WO | WO 97/07139 | 2/1997 | |
| WO | WO/97/07139 A2 * | 2/1997 | ............ C08B 37/00 |
| WO | WO 97/07139 A2 * | 2/1997 | ............ C08B 37/00 |
| WO | WO 00/30609 A1 * | 2/2000 | ............ A61K 9/00 |
| WO | WO 00/30609 | 6/2000 | |

OTHER PUBLICATIONS

Written Opinion in International Application No. PCT/IB2015/058300, Jan. 22, 2016, pp. 1-5.
Aiba, S.-I. "Studies on chitosan: 1. Determination of the degree of N-acetylation of chitosan by ultraviolet spectrophotometry and gel permeation chromatography" *International Journal of Biological Macromolecules*, Jun. 1986, pp. 173-176, vol. 8.
Balázs, N. et al. "Limitations of pH-potentiometric titration for the determination of the degree of deacetylation of chitosan" *Carbohydrate Research*, 2007, pp. 124-130, vol. 342.
Baxter, A. et al. "Improved method for i.r. determination of the degree of N-acetylation of chitosan" *International Journal of Biological Macromolecules*, Jun. 1992, pp. 166-169, vol. 14.
Brugnerotto, J. et al. "An infrared investigation in relation with chitin and chitosan characterization" *Polymer*, 2001, pp. 3569-3580, vol. 42.
Curotto, E. et al. "Quantitative Determination of Chitosan and the Percentage of Free Amino Groups" *Analytical Biochemistry*, 1993, pp. 240-241, vol. 211.
Domard, A. "Determination of N-acetyl content in chitosan samples by c.d. measurements" *International Journal of Biological Macromolecules*, Dec. 1987, pp. 333-336, vol. 9.
Gupta, K. C. et al. "Effects of degree of deacetylation and cross-linking on physical characteristics, swelling and release behavior of chitosan microspheres" *Carbohydrate Polymers*, 2006, pp. 43-54, vol. 66.

(Continued)

*Primary Examiner* — Ganapathy Krishnan
(74) *Attorney, Agent, or Firm* — Saliwanchik, Lloyd & Eisenschenk

(57) ABSTRACT

The present invention relates to a heat-sterilized aqueous composition comprising a solubilized chitosan and glycerol. It also relates to a process of preparation of the same, as well as the use thereof, including compositions useful for the prevention and treatment of dry eye syndrome and arthritic diseases or disorders.

8 Claims, 3 Drawing Sheets

(56) References Cited

OTHER PUBLICATIONS

Jarry, C. et al. "Irradiating or Autoclaving Chitosan/Polyol Solutions: Effect on Thermogelling Chitosan-β-glycerophosphate Systems" *Chemical and Pharmaceutical Bulletin*, Oct. 2002, pp. 1335-1340, vol. 50, No. 10.

Nanjo, F. et al. "Enzaymatic Method for Determination of the Degree of Deacetylation of Chitosan" *Analytical Biochemistry*, 1991, pp. 164-167, vol. 193.

Nguyen, S. et al. "Improved reproducibility in the determination of the molecular weight of chitosan by analytical size exclusion chromatography" *Carbohydrate Polymers*, 2009, pp. 528-533, vol. 75.

Nwe, N. et al. "Production of Fungal Chitosan by Enzymatic Method and Applications in Plant Tissue Culture and Tissue Engineering: 11 Years of Our Progress, Present Situation and Future Prospects" *Biopolymers*, 2010, pp. 135-162, Chapter 7.

Pochanavanich, P. et al. "Fungal chitosan production and its characterization" *Letters in Applied Microbiology*, 2002, pp. 17-21, vol. 35.

Tan, S. C. et al. "The degree of deacetylation of chitosan: advocating the first derivative UV-spectrophotometry method of determination" *Talanta*, 1998, pp. 713-719, vol. 45.

Zhang, Y. et al. "Determination of the degree of deacetylation of chitin and chitosan by X-ray powder diffraction" *Carbohydrate Research*, 2005, pp. 1914-1917, vol. 340.

\* cited by examiner

HEAT-STERILIZED FORMULATION COMPRISING CHITOSAN AND PROCESS OF PREPARATION THEREOF

CROSS-REFERENCE TO RELATED APPLICATION

This application is the U.S. national stage application of International Patent Application No. PCT/IB2015/058300, filed Oct. 28, 2015.

FIELD OF THE INVENTION

The present invention relates to a novel composition comprising chitosan that forms a clear, viscous and stable solution at a pH approaching neutral pH after heat-sterilization, and to a process for producing the same.

BACKGROUND OF THE INVENTION

Chitosan is known as a chitin derivative obtained by partial to substantial alkaline N-deacetylation of chitin also named poly(N-acetyl-D-glucosamine), which is a naturally occurring biopolymer.

Chitosan contains free amine ($-NH_2$) groups and acetyl groups and may be characterized as to the proportion of N-acetyl-D-glucosamine units and D-glucosamine units, and such is expressed as the degree of deacetylation (DD) of the fully acetylated polymer chitin.

Parameters of chitosan influencing important properties such as solubility and viscosity are the degree of deacetylation (DD) which may be understood as representing the percentage of deacetylated monomers, and the average molecular weight (MW). Chitosan is known to be biodegradable, biocompatible, bioadhesive, bacteriostatic, and further to be able to promote wound-healing, drug absorption, and tissue reconstruction. Due to its above mentioned intrinsic properties, chitosan has found numerous cosmetic and pharmaceutical applications, for instance ophthalmic applications, in regenerative medicine, or for wound healing.

Therefore, considering the advantageous properties of chitosan and its numerous applications, there have been many attempts to produce sterile and stable compositions comprising chitosan.

WO 97/007139 discloses a process for sterilizing a polysaccharide composition containing water-insoluble chitosan without substantially degrading the polysaccharide. In this process, water-insoluble chitosan is first dispersed in water, then sterilized under high pressure steam to form a chitosan suspension with a pH equal to or higher than about 7. The suspended chitosan particles of said suspension are finally dissolved in an aseptic acid to decrease the final pH and form a sterilized chitosan solution.

Jarry et al. 2002, *Chem. Pharm. Bull.*, 50(10): 1335-1340 disclose a composition containing a chitosan free base dissolved in HCl and glycerol, having a final pH of about 5.25 after autoclaving. Addition of glycerophosphate to this solution increases the pH to about 7.14 and produces a turbid solution (presence of precipitates).

Despite the development of sterile compositions comprising chitosan, there is a continuous need to further improve the properties of known chitosan compositions, in particular to provide aqueous formulations containing chitosan having a pH close to the neutral pH, which are stable, clear, and viscous after heat sterilization and which are suitable for pharmaceutical use.

SUMMARY OF THE INVENTION

The present invention is directed towards a process for preparing a heat-sterilized composition comprising chitosan and glycerol that forms a clear and viscous solution at a pH close to neutral pH after heat sterilization, as well as to compositions obtainable by said process. In particular, the present invention relates to the unexpected finding that solubilizing a water-insoluble chitosan (amine chitosan) before heat-sterilization according to a process of the invention avoids the formation of aggregates and allows the preparation of clear solutions suitable for ophthalmic use. According to a particular aspect of the invention, it is advantageous to avoid the formation of aggregates in a solution containing a water-insoluble chitosan (amine chitosan) before heat-sterilization since heat-sterilization of already formed aggregates render the removal of those aggregates difficult to achieve, time consuming and costly. A first aspect of the invention relates to a process for preparing a heat-sterilized aqueous composition comprising solubilized chitosan and glycerol, wherein said composition is a clear and viscous solution, at a pH between 6 and 7.5, in particular between 6 and 7, wherein said process comprises the following steps:
  (i) Solubilizing chitosan having an average molecular weight ranging from 10 kDa to 250 kDa and a degree of deacetylation higher than 60% in an aqueous solution of weak acid comprising a carboxylic group;
  (ii) Adding glycerol;
  (iii) Adjusting the pH to a pH value between 6 and 7.5 by addition of an aqueous solution of weak base; and
  (iv) Steam sterilizing;
  thereby forming a heat-sterilized composition comprising solubilized chitosan and glycerol that is a clear and viscous solution at a pH between 6 and 7.5.

A second aspect of the invention relates to a heat-sterilized aqueous composition comprising solubilized chitosan and glycerol obtainable by the process of preparation described herewith, and in particular to a pharmaceutical composition comprising said heat-sterilized aqueous composition and at least one pharmaceutically acceptable carrier, diluent or excipient thereof.

A third aspect of the invention provides a heat-sterilized aqueous composition comprising a solubilized chitosan and glycerol, wherein said composition has a pH comprised between 6 and 7.5, and forms a clear and viscous solution.

In a fourth aspect, a composition as described herewith is for use as a medicament, in particular as an ophthalmic composition.

A fifth aspect of the invention relates to a composition as described herewith for use in treatment of dry eye syndrome, Sjögren's syndrome bacterial infections on the surface of the eye or related anterior structures of the eye.

A sixth aspect of the invention provides a composition as described herewith for use in the treatment of an arthritic disease.

A seventh aspect of the invention relates to the use of a composition as described herewith for the manufacture of a medicament for treating dry-eye syndrome, Sjögren's syndrome bacterial infections on the surface of the eye or related anterior structures of the eye.

An eighth aspect of the invention provides the use of a composition as described herewith for the manufacture of a medicament for treating an arthritic disease.

A ninth aspect of the invention further relates to a method for preventing and/or treating dry eye syndrome, Sjögren's syndrome bacterial infections on the surface of the eye or related anterior structures caused by bacteria sensitive to chitosan, and/or an arthritic disease, comprising administering, in a subject in need thereof, a therapeutically effective amount of a composition as described herewith.

Other features and advantages of the invention will be apparent from the following detailed description.

DETAILED DESCRIPTION OF THE INVENTION

Figure 1:
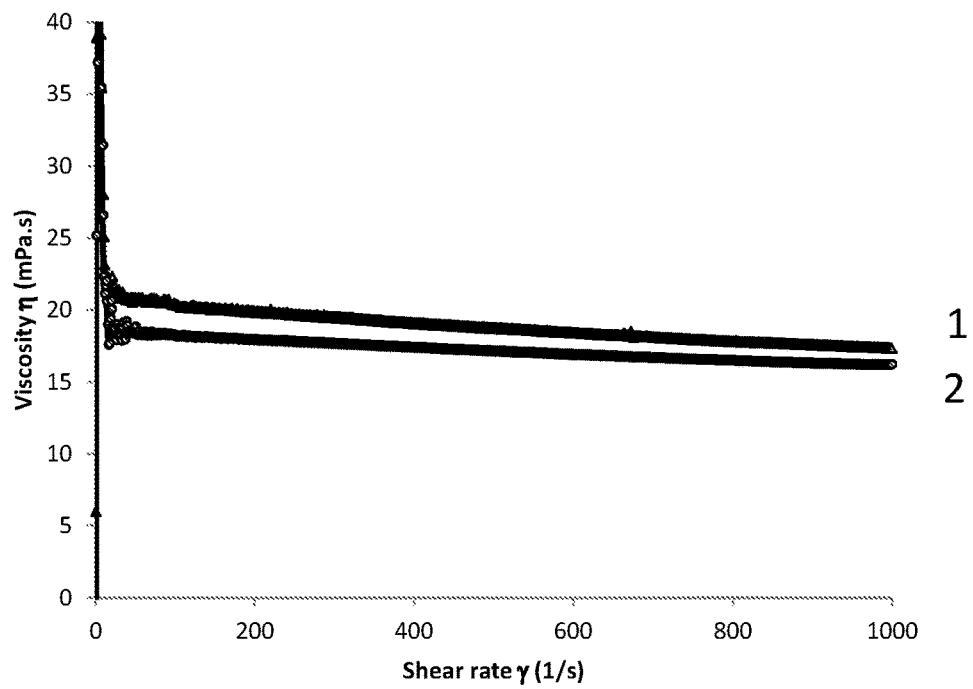
FIG. 1: rheological profile of the composition comprising 0.5% chitosan and glycerol according to Example 2 before (1) and after (2) heat sterilization.

Chitosan is a linear polysaccharide composed of randomly distributed β-(1-4)-linked D-glucosamine (deacetylated unit) and N-acetyl-D-glucosamine (acetylated unit). It can be obtained by partial to substantial deacetylation of chitin also named poly(N-acetyl-D-glucosamine), which is a naturally occurring biopolymer found in shellfish and fungi, typically by treating shrimp and other crustacean shells or fungi cell wall with the alkali sodium hydroxide. Alternatively, chitosan can be extracted from naturally occurring chitosan present in the cell wall of fungi such as *Mucor*, *Absidia* and *Rhizopus* genera. According to a particular aspect, the chitosan of the invention is of fungal origin.

The term "Degree of deacetylation" ("DD") applied to a sample of chitosan means the relative average amount of D-glucosamine units over the total of average amounts of N-acetyl-D-glucosamine units and D-glucosamine units present in the macromolecular chain of chitosan sample.

Several methods can be used to determine the degree of deacetylation (DD) of chitosan. These methods include ninhydrin test (Curotto and Aros, 1993, *Analytical Biochemistry*, 211 (2): 240-241), infrared spectroscopy (IR) (Brugnerotto et al. 2001, *Polymer*, 42 (8): 3569-3580), linear potentiometric titration (LPT) (Balázs and Sipos, 2007, *Carbohydrate Research*, 342 (1): 124-130), circular dichroism spectroscopy (Domard 1987, *International Journal of Biological Macromolecules*, 9 (6): 333-336), hydrogen bromide titrimetry (Baxter et al., 1992, *International Journal of Biological Macromolecules*, 14 (3): 166-169), GPC (Alba, 1986, *International Journal of Biological Macromolecules*, 8 (3): 173-176), ultraviolet (UV) spectroscopy (Tan et al., 1998, *Talanta*, 45 (4): 713-719), nuclear magnetic resonance spectroscopy (NMR) (Zhang et al., 2005, *Carbohydrate Research*, 340 (11): 1914-1917), enzymatic determination (Nanjo et al., 1991, *Analytical Biochemistry*, 193 (2): 164-167) and elemental analysis (Gupta and Jabrail, 2006, *Carbohydrate Polymers*, 66 (1): 43-54). The term "Degree of acetylation" ("DA") refers to the relative average amount of N-acetyl-D-glucosamine units over the total of average amounts of N-acetyl-D-glucosamine units and D-glucosamine units present in the macromolecular chain of chitosan sample.

The term "weak" acid is well known to the skilled person and indicates an acid that is only partially ionized in solution. Weak acids according to the invention include lactic acid, gluconic acid, and succinic acid, sorbic acid and citric acid. Weak acids according to the invention further include galactic acid.

The term "weak" base is well known to the skilled person and indicates a base that is only partially ionized in solution. Weak bases according to the invention include sodium succinate, sodium lactate, potassium sorbate and potassium gluconate.

The term "steam sterilizing" according to the invention indicates sterilizing conditions according to the European Pharmacopoeia guidelines, such as autoclaving according to the same.

"Dry eye syndrome" may also be called "dry eye" or "keratoconjunctivitis sicca" (KCS) or "ocular surface disease". Dry eye syndrome may result in disruption of the ocular surface, causing a variety of symptoms and signs and interference with quality of life. A person with dry eye syndrome may experience dry, gritty/scratchy, or filmy feeling, burning or itching, redness of the eyes (conjunctivitis), blurred vision, foreign body sensation, and light sensitivity. Dry eye syndrome generally results from decreased tear production, excessive tear evaporation, and an abnormality in the production of mucus or lipids normally found in the tear layer, or a combination of these.

The term "blepharitis" designates the inflammation of the eyelid margins that may be acute (ulcerative or nonulcerative) or chronic (meibomian gland dysfunction, seborrheic blepharitis). Symptoms and signs include itching and burning of the eyelid margins with redness and edema. Acute ulcerative blepharitis is usually caused by bacterial infection (usually staphylococcal) of the eyelid margin at the origins of the eyelashes; the lash follicles and the meibomian glands are also involved. Acute ulcerative blepharitis may also be due to a virus (e.g. herpes simplex, varicella zoster). Acute nonulcerative blepharitis is usually caused by an allergic reaction involving the same area (e.g. atopic blepharodermatitis and seasonal allergic blepharoconjunctivitis, which cause intense itching, rubbing, and a rash; or contact sensitivity in case of dermatoblepharoconjunctivitis). Chronic blepharitis is noninfectious inflammation of unknown cause. Meibomian glands in the eyelid produce lipids (meibum) that reduce tear evaporation by forming a lipid layer on top of the aqueous tear layer. In meibomian gland dysfunction, the lipid composition is abnormal, and gland ducts and orifices can become obstructed with hard, waxy plugs. Secondary bacterial colonization often occurs on the scales that develop on the eyelid margin. Meibomian glands can become obstructed. Most patients with meibomian gland dysfunction or seborrheic blepharitis have increased tear evaporation and secondary keratoconjunctivitis sicca.

The term "arthritic diseases or disorders" designates herewith a complex family of musculoskeletal disorders consisting of more than 100 different diseases or conditions that destroy joints, bones, muscles, cartilage and other connective tissues, hampering or halting physical movement. It designates more specifically those conditions which cause inflammation or damage to the joints, muscles or other tissues. This term includes osteoarthritis, rheumatoid arthritis, psoriatic arthritis, juvenile arthritis.

The term "pharmaceutically acceptable" refers to a carrier comprised of a material that is not biologically or otherwise undesirable.

The term "carrier" refers to any components present in a pharmaceutical formulation other than the active agent and thus includes diluents, binders, lubricants, disintegrants, fillers, coloring agents, wetting or emulsifying agents, pH buffering agents, preservatives and the like.

The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "efficacy" of a treatment or method according to the invention can be measured based on changes in the course of disease or condition in response to a use or a method according to the invention. For example, the efficacy of a treatment of dry eye syndrome according to the invention can be measured by its impact on eye dryness, gritty/scratchy feeling, filmy feeling, burning or itching, redness of the eyes, blurred vision, foreign body sensation, and light sensitivity, tear break up time (tBUT), fluorescein staining, measurement of the tear osmolarity.

The term "effective amount" as used herein refers to an amount of a composition according to the invention, or a pharmaceutical formulation thereof, that elicits a detectable reduction of the symptoms of the disease in a subject that is being administered said composition, these symptoms can include, for instance, dryness of the eye, gritty/scratchy feeling, or filmy feeling, burning or itching, redness of the eyes, blurred vision, foreign body sensation, and light sensitivity in the case of dry eye syndrome, or a detectable reduction of inflammation or damage to the joints or muscles in the case of an arthritic disease.

The term "subject" as used herein refers to mammals. For examples, mammals contemplated by the present invention include human, primates, domesticated animals such as cattle, sheep, pigs, horses laboratory rodents and the like.

Process of Preparation According to the Invention

A first aspect of the invention provides a process for preparing a heat-sterilized aqueous composition comprising solubilized chitosan and glycerol, wherein said composition is a clear and viscous solution at a pH close to neutral pH, for instance comprised between 6 and 7.5, wherein said process comprises the following steps:
(i) Solubilizing chitosan having an average molecular weight ranging from 10 kDa to 250 kDa and a degree of deacetylation higher than 60% in an aqueous solution of weak acid comprising a carboxylic group;
(ii) Adding glycerol;
(iii) Adjusting the pH close to neutral pH, for instance to a pH comprised between 6 and 7.5, by addition of an aqueous solution of weak base; and
(iv) Steam sterilizing;
thereby forming a heat-sterilized composition comprising solubilized chitosan and glycerol that is a clear and viscous solution at said pH.

In a particular embodiment of the invention, is provided a process as described above for preparing a heat-sterilized aqueous composition comprising solubilized chitosan and glycerol, wherein, in step (i), the molar ratio between the carboxyl group (—COOH) of said weak acid and the amine group (—NH$_2$) of said chitosan is comprised between 1:0.9 and 1:1.1, and in particular is of about 1:1 or 1:1.05.

The concentration of amine group (—NH$_2$) of said chitosan depends on the DD of the chitosan. For instance, for a chitosan having a DD of 65 mol (%), there are 65 mol (%) of amine group (—NH$_2$) that can react with the carboxyl group of said weak acid. The remaining 35 mol (%) corresponds to the acetyl group (—COCH$_3$) of chitosan.

For instance, in a particular embodiment of the process according to the invention, in step (i), a chitosan having a MW of 173 kDa and a degree of acetylation of 35% (mol) is solubilized at a final concentration of 0.5% (w/w) in an aqueous solution of lactic acid, as weak acid, at a final concentration of 0.175% (w/w).

Without being linked to any particular theory, the inventors of the present invention observed that a molar ratio between the carboxyl group (—COOH) of said weak acid and the amine group (—NH$_2$) of said chitosan in the range indicated herewith improves solubilization of the chitosan in the aqueous solution of the weak acid and improves the stability of the composition of the invention.

In a particular embodiment of the process for preparing a heat-sterilized composition comprising chitosan and glycerol according to the invention, solubilizing chitosan is carried out at room temperature by stirring.

In a particular embodiment of the process for preparing a heat-sterilized composition comprising chitosan and glycerol according to the invention, said weak acid of step (i) is selected among lactic acid, gluconic acid, and succinic acid, sorbic acid, citric acid and/or said weak base of step (iii) is selected among sodium succinate, sodium lactate, potassium sorbate and potassium gluconate.

In another particular embodiment, is provided a process for preparing a heat-sterilized aqueous composition comprising solubilized chitosan and glycerol, wherein said sterilized composition is a clear and viscous solution at a pH comprised between 6 and 7.5, wherein said process comprises the following steps:
(i) Solubilizing chitosan having an average molecular weight ranging from about 150 to about 180 kDa and a degree of deacetylation higher than 60% (mol) such as between 60% and 75% (mol) in an aqueous solution of lactic acid, wherein the molar ratio between the carboxyl group (—COOH) of said weak acid and the amine group (—NH$_2$) of said chitosan is comprised between 1:0.9 and 1:1.1, including about 1:1 or 1:1.05;
(ii) Adding glycerol;
(iii) Adjusting the pH to a value comprised between 6 and 7.5 by addition of an aqueous solution of sodium succinate; and
(iv) Autoclaving at 121° C. for 15 min;
thereby forming a heat-sterilized composition comprising solubilized chitosan and glycerol that is a clear and viscous solution.

In a further particular embodiment of the invention, is provided a process as described above for preparing a heat-sterilized aqueous composition comprising solubilized chitosan and glycerol, wherein:
in step (i), said chitosan is present at a concentration comprised between 0.05 and 3% (w/w), in particular between 0.3 and 0.75% (w/w), more particularly about 0.5% (w/w), and said weak acid is lactic acid present at a concentration comprised between 0.12% and 0.22% (w/w), in particular between 0.16% and 0.19% (w/w), wherein the molar ratio between the carboxyl group (—COOH) of said weak acid and the amine group (—NH$_2$) of said chitosan is of about 1:1.05, in step (ii), said glycerol is present at a concentration comprised between 0.4 and 1% (w/w), in particular between 0.4 and 0.6% (w/w), or about 0.4% (w/w) such as 0.36% (w/w), 0.37% (w/w), 0.38% (w/w), 0.39% (w/w), 0.40% (w/w), 0.41% (w/w), 0.42% (w/w), 0.43% (w/w), 0.44% (w/w) or 0.45% (w/w), or about 0.5% (w/w) such as 0.46% (w/w), 0.47% (w/w), 0.48% (w/w), 0.49% (w/w), 0.50% (w/w), 0.51% (w/w), 0.52% (w/w), 0.53% (w/w), 054% (w/w), 0.55% (w/w), in step (iii) said weak base is sodium succinate present at a concentration comprised between 1.0 and 1.7% (w/w), in particular about 1.4% (w/w).

In a still further embodiment of the invention is provided a process for preparing a heat-sterilized aqueous composition comprising solubilized chitosan and glycerol, wherein said composition is a clear and viscous solution at a pH comprised between 6 and 7.5, wherein said process comprises the steps of:

(i) Solubilizing chitosan having an average molecular weight between 150,000-180,000 Da and a degree of deacetylation comprised between 65% (mol) and 70% (mol), at a concentration of about 0.5% (w/w) in an aqueous solution of lactic acid at a concentration comprised between 0.12 and 0.22% (w/w) or about 0.16%, about 0.17%, about 0.18%, or about 0.19% (w/w);

(ii) Adding glycerol at a final concentration comprised between 0.4 and 1% (w/w), in particular between 0.4 and 0.6% (w/w), or about 0.4% (w/w) such as 0.36% (w/w), 0.37% (w/w), 0.38% (w/w), 0.39% (w/w), 0.40% (w/w), 0.41% (w/w), 0.42% (w/w), 0.43% (w/w), 0.44% (w/w) or 0.45% (w/w), or about 0.5% (w/w) such as 0.46% (w/w), 0.47% (w/w), 0.48% (w/w), 0.49% (w/w), 0.50% (w/w), 0.51% (w/w), 0.52% (w/w), 0.53% (w/w), 054% (w/w), 0.55% (w/w);

(iii) Adjusting the pH to about 6.5 by addition of an aqueous solution of sodium succinate at a final concentration of about 1.40% (w/w);

(iv) Autoclaving at 121° C. for 15 min;

thereby forming a heat-sterilized composition that is a clear and viscous (for instance a viscosity of about 18 mPas·s) solution.

In a further embodiment of the process according to the invention, chitosan of step (i) is an amine form of chitosan.

In a further embodiment of the process according to the invention, chitosan of step (i) is a chitosan base.

In a further embodiment of the process according to the invention, chitosan of step (i) is of animal origin.

In a further embodiment of the process according to the invention, chitosan of step (i) is of fungal origin, in particular from *Agaricus bisporus*.

In a further embodiment of the process according to the invention, chitosan of step (i) is a chitosan amine of fungal origin, in particular from *Agaricus bisporus*.

In a still further embodiment, the process according to the invention may further comprise a step of solubilizing pullulan, in particular pullulan having a MW ranging from 10 to 3,000 kDa, in an aqueous solution of weak acid such as lactic acid, before the steps of adding glycerol, adjusting the pH and autoclaving, thereby forming a heat-sterilized composition comprising chitosan and pullulan that is a clear and viscous solution at a pH comprised between 6 and 7.5, in particular between 6 and about 7.

In a still another further embodiment, the process according to the invention further comprises a preliminary step of providing a solubilized pullulan, in particular pullulan having a MW ranging from about 10 to about 3,000 kDa, in an aqueous solution of weak acid such as lactic acid, into which the chitosan is solubilized under step (i) before the steps of adding glycerol.

In a particular embodiment, the heat-sterilized composition comprising solubilized chitosan and glycerol obtained by the process according to the invention is a stable, clear, colorless, and viscous solution.

Compositions of the Invention

In another aspect of the invention is provided a heat-sterilized aqueous composition comprising solubilized chitosan and glycerol obtainable by the process of preparation described herewith.

Said composition is a clear and viscous solution, at a pH comprised between 6 and 7.5, in particular at a pH comprised between 6 and about 7.

In an advantageous embodiment, said composition is stable, meaning that the chitosan polymer is not substantially degraded and that the solution maintains its viscosity and appearance after heat sterilization and/or storage.

In a particular embodiment, said composition comprises a chitosan having an average Molecular Weight (MW) ranging from about 150 to about 180 kDa and a degree of deacetylation (DD) comprised between 60% (mol) and 75% (mol).

In another embodiment, said composition comprises a chitosan of fungal origin such as from *Agaricus bisporus*.

In another embodiment, said composition comprises chitosan present in the amine form.

In a still other embodiment, said composition comprises a chitosan base.

In a specific embodiment, the heat-sterilized aqueous composition comprising solubilized chitosan and glycerol obtainable by the process of preparation described herewith exhibits at least one of the following features:

said composition has a viscosity comprised between 10 and 500 mPa·s.

said composition has an osmolality comprised between 150 and 350 mOsm/kg.

said composition exhibits a non-Newtonian rheological behaviour, said composition has antimicrobial activity and/or anti-lipase activity.

In a further aspect, the invention provides a heat-sterilized aqueous composition comprising a solubilized chitosan and glycerol, wherein said composition has a pH comprised between 6 and 7.5, and forms a clear and viscous solution at said pH, in particular after heat-sterilization.

In a particular embodiment, the composition according to the invention forms a clear solution meaning that substantially no visible particles in suspension are present in said composition.

In a particular embodiment, the composition according to the invention is stable after heat sterilization, meaning that the chitosan polymer is not substantially degraded after sterilization and/or storage.

In a particular aspect, the invention provides a heat-sterilized aqueous composition comprising a solubilized chitosan and glycerol, wherein said chitosan has an average molecular weight ranging from about 10 kDa to about 250 kDa and a degree of deacetylation higher than 60%, and wherein said composition has a pH comprised between 6 and 7.5, in particular between 6 and about 7, and forms a stable, clear and viscous solution at said pH after heat-sterilization.

In a particular embodiment, the composition according to the invention is a pharmaceutical composition comprising a heat-sterilized aqueous composition comprising a solubilized chitosan and glycerol as described herewith and at least one pharmaceutically acceptable carrier, diluent or excipient thereof.

In a further particular embodiment, the heat-sterilized aqueous composition according to the invention further comprises a pullulan.

In a further particular embodiment, the heat-sterilized aqueous composition according to the invention further comprises a pullulan having a molecular weight ranging from about 10 to about 3,000 kDa.

In a further particular embodiment, the heat-sterilized aqueous composition according to the invention further comprises a pullulan having a molecular of about 10 kDa.

In a further particular embodiment, the heat-sterilized aqueous composition according to the invention further comprises a pullulan at a concentration ranging from about 0.5 to about 3%.

In a particular aspect, the composition according to the invention is for use as a medicament, more particularly as an ophthalmic composition.

In a particular embodiment, the heat-sterilized aqueous composition according to the invention is an ophthalmic composition for topical use.

In another particular embodiment, the heat-sterilized aqueous composition according to the invention is an intra-articular composition.

In a further aspect, the invention provides the use of a heat-sterilized aqueous composition according to the invention for the preparation of a pharmaceutical formulation, in particular an ophthalmic composition or an intra-articular composition.

Thus, one other particular aspect, relates to an aqueous ophthalmic composition comprising a solubilized chitosan and glycerol, wherein said chitosan has an average molecular weight ranging from about 10 kDa to about 250 kDa and a degree of deacetylation higher than 60%, and wherein said composition has a pH comprised between 6 and 7.5, and forms a clear and viscous solution at said pH, even after heat-sterilization.

In a particular embodiment, is provided an ophthalmic heat-sterilized aqueous composition comprising a solubilized chitosan and glycerol, wherein said chitosan has an average molecular weight ranging from about 150 to 180 kDa and a degree of deacetylation (DD) comprised between 60% (mol) and 75% (mol).

In a particular embodiment of said composition, said chitosan is present in the amine form and/or is of fungal origin such as from *Agaricus bisporus*.

In a particular embodiment, said composition has a viscosity comprised between 10 and 500 mPa·s., an osmolality comprised between 150 and 350 mOsm/kg (for example from about 250 to 300 mOsm/kg), and exhibits a non-Newtonian rheological behaviour, antimicrobial activity and/or anti-lipase activity.

According to a particular aspect of the invention is provided a process or a formulation of the invention where the weak acid is lactic acid.

According to a particular aspect of the invention is provided a process or a formulation of the invention where the base acid is selected from sodium succinate and potassium sorbate.

In another particular embodiment of said composition, said chitosan is present at a concentration ranging from about 0.05 to about 3% (w/w), said glycerol is present at a concentration ranging from 0.2 to 2% (w/w), based on the total composition. According to a particular embodiment, the composition of the invention is an ophthalmic composition and glycerol is present at a concentration ranging from 0.2 to 1% (w/w) based on the total composition.

In another particular embodiment of said composition, the molar ratio between the carboxyl group (—COOH) of said weak acid and the amine group (—$NH_2$) of said chitosan is comprised between 1:0.9 and 1:1.1, and in particular is of about 1:1 or 1:1.05.

In another particular embodiment, said composition further comprises lactic acid at a concentration comprised between about 0.12 and about 0.22% (w/w), and sodium succinate at a concentration comprised between 1.0 and 1.7% (w/w).

In a further particular embodiment, said composition further comprises a polymer selected from the group consisting of: a pullulan and alginate.

Another particular aspect, relates to an aqueous composition for intra-articular injections, comprising a solubilized chitosan and glycerol, wherein said chitosan has an average molecular weight ranging from about 10 kDa to about 250 kDa and a degree of deacetylation higher than 60%, and wherein said composition has a pH comprised between 6 and 7.5, in particular between 6 and about 7, and forms a clear and viscous solution at said pH, even after heat-sterilization.

In one embodiment of the different aspects of the invention, the chitosan used in the present invention has an average Molecular Weight (MW) ranging from about 10 kDa to about 250 kDa, in particular from about 20 kDa to about 220 kDa, more particularly from about 50 kDa to about 220 kDa, more particularly from about 100 kDa to about 220 kDa, still more particularly from about 140 kDa to about 200 kDa, still more particularly from about 150 to about 180 kDa, still more particularly from about 159 kDa to about 175 kDa, or about 155 kDa, 156 kDa, 157 kDa, 158 kDa, 159 kDa, 160 kDa, 161 kDa, 162 kDa, 163 kDa, 164 kDa, 165 kDa, 166 kDa, 167 kDa, 168 kDa, 169 kDa, 170 kDa, 171 kDa, 172 kDa, 173 kDa, 174 kDa, or 175 kDa.

The average molecular weight of chitosan used in the present invention may be determined by size exclusion chromatography (Nguyen et al., 2009, *Carbohydrate Polymer*, 75, 528-533).

In another embodiment, the chitosan used in the present invention has a degree of deacetylation (DD) higher than 60%, in particular comprised between 60% (mol) and 90% (mol), more particularly between 60% (mol) and 80% (mol), still more particularly between 60% (mol) and 75% (mol), still more particularly between 65% (mol) and 70% (mol), or about 65% (mol) or about 70% (mol), which corresponds to a degree of acetylation (DA) lower than 40%, in particular comprised between 10% (mol) and 40% (mol), more particularly between 20% (mol) and 40% (mol), still more particularly between 25% (mol) and 40% (mol), still more particularly between 30% (mol) and 35% (mol), or about 30% (mol) or 35% (mol), respectively.

In a further embodiment, the chitosan is of animal origin including crustaceans such as crabs, shrimp, squid bone plates and cuttlefishes, and insects.

In a further embodiment, the chitosan is of fungal origin. The mycelia of various fungi including Ascomycetes, Zygomycetes, Basidiomycetes and Deutermoycetes, are alternative sources of chitin and chitosan (Pochanavanich and Suntornsuk, 2002, *Lett. in Appl. Microbiol.*, 35: 17-21). For instance, said chitosan comprised in the composition of the invention can be extracted from mushrooms including *Agaricus bisporus, Agaricus hortensis, Armilla mellea, Aspergillus niger, Auricularia auriculajudae, Gongronella butleri, Lentinula edodes, Mucor rouxii, Pleurotus ostreatus, Pleu-*

*rotus sajo-caju*, *Pleurotus eryngii*, *Trametes versicolor*, especially from *Agaricus bisporus* (*A. bisporus*) also called "white mushroom", by methods well known in the art such as a typical extraction procedure consisting of three steps: (1) alkaline treatment to remove protein and alkali soluble polysaccharides; (2) acid reflux to separate chitin and chitosan; and (3) precipitation of chitosan under alkaline conditions. Removal of proteins by alkaline treatment is commonly performed with 1N NaOH at 95° C. from 1 to 6 h or at 121° C. from 0.25 h to 1 h. Separation of chitosan by acid treatment is usually carried out by 2 to 10% acetic or hydrochloric acid at 95° C. for 3 to 14 h. Alternative methods for producing chitosan include the enzymatic method described in Nwe et al., 2010, *Biopolymers, Magdy Elnashar Editor, chapter* 7: 135-162.

The composition according to the invention advantageously comprising a chitosan of fungal origin exhibits advantageous properties such as the absence of animal proteins, a lower variability in terms of molecular weight and degree of deacetylation compared to chitosan of animal origin.

Said composition of the invention further advantageously exhibits antimicrobial activity, in particular antistatic or bactericidal activity.

Said composition of the invention advantageously exhibit anti-lipase activity.

In another particular embodiment, the amine form of chitosan (chitosan containing free amine groups ($-NH_2$)) is used in the present invention.

In another particular embodiment, the chitosan base is used in the present invention.

In a particular embodiment, the composition of the invention has a pH comprised between 6 and 7.5, in particular between 6 and about 7, more particularly between 6.5 and about 7, for instance about 6.5.

In another embodiment, the composition according to the invention comprises a chitosan at a concentration ranging from about 0.05 to about 3% (w/w) based on the total composition, in particular from about 0.2 to about 1% (w/w), more particularly from about 0.5 to about 0.75% (w/w), or about 0.5% (w/w).

For the purpose of the invention, the concentration of chitosan is adjusted according to the average molecular weight and degree of deacetylation of the chitosan used and according to the desired viscosity of the composition.

Typically, the composition of the invention has a viscosity comprised between 10 and 500 mPa·s, for instance between 10 and 100 mPa·s or about 20 mPa·s such as 16, 17, 18, 19, 20, 21, 22, 23, 24 mPa·s.

Typically, the composition of the invention shows pseudoplastic and viscoelastic properties.

These properties make the compositions according to the invention particularly adapted for applications as artificial tears in ophthalmic applications and for intra-articular injections for regenerative medicine.

Typically, the composition of the invention exhibits a non-Newtonian rheological behaviour. This rheological behaviour makes the composition of the invention particularly appropriate for use in ophthalmic applications, for instance as artificial tears for treating dry eye syndrome.

In one embodiment, the concentration of glycerol in the composition according to the invention is comprised between 0.2 and 2% (w/w), in particular between 0.4 and 1% (w/w), more particularly between 0.4 and 0.6% (w/w), or about 0.4% (w/w) such as 0.36% (w/w), 0.37% (w/w), 0.38% (w/w), 0.39% (w/w), 0.40% (w/w), 0.41% (w/w), 0.42% (w/w), 0.43% (w/w), 0.44% (w/w) or 0.45% (w/w), or about 0.5% (w/w) such as 0.46% (w/w), 0.47% (w/w), 0.48% (w/w), 0.49% (w/w), 0.50% (w/w), 0.51% (w/w), 0.52% (w/w), 0.53% (w/w), 054% (w/w), 0.55% (w/w).

In the composition according to the invention, glycerol reduces the stickiness of the composition and may act as a protector of chitosan during steam sterilization. Glycerol may also act as osmotic agent and play a role on the osmoprotection of the composition according to the invention.

Typically, the osmolality of the composition according to the invention is comprised between 150 and 350 mOsm/kg, more particularly between 240 and 340 mOsm/kg, for instance about 280 or 300 mOsmol/kg.

In a further embodiment, the composition of the invention is stable and clear at a pH close to neutral pH of 7, for instance at a pH higher than 6, higher than 6.2, about 6.5, higher than 6.5, about 7, or comprised between 6.5 and about 7.

One of the advantages of the composition according to the invention is that it forms a stable and clear solution after autoclaving at a pH close to the physiological pH of 7.4, or close to neutral pH, without the need of adding a base which typically leads to the precipitation of chitosan in the case of compositions and process of the prior art.

In a particular embodiment, the composition of the invention forms a stable, clear and viscous solution at said pH after heat-sterilization including sterilization by autoclaving, for instance at 121° C. for 15 min. More particularly, the composition of the invention forms a stable, clear, colorless, and viscous solution at said pH after heat-sterilization.

Therapeutic Applications

Another aspect of the invention relates to a composition, in particular an ophthalmic composition, as described herewith for use in treatment of dry eye syndrome, in particular dry eye with blepharitis, eye irritation caused by environmental conditions or contact lenses, keratoconjunctivitis sicca, Sjögren's syndrome, bacterial infections on the surface of the eye or related anterior structures caused by bacteria sensitive to chitosan.

In a still other aspect of the invention, is provided a composition as described herewith for use in the treatment of an arthritic disease including osteoarthritis, and psoriatic arthritis.

Another aspect of the invention provides the use of a composition as described herewith for the manufacture of a medicament for treating dry-eye syndrome, in particular dry eye with blepharitis, eye irritation caused by environmental conditions or contact lenses, keratoconjunctivitis sicca, Sjögren's syndrome bacterial infections on the surface of the eye or related anterior structures caused by bacteria sensitive to chitosan.

In a still other aspect of the invention, it is provided the use of a composition as described herewith for the manufacture of a medicament for treating an arthritic disease including osteoarthritis, rheumatoid arthritis, psoriatic arthritis, juvenile arthritis.

In a further aspect of the invention is provided a method for preventing and/or treating dry eye syndrome including dry eye syndrome with blepharitis, eye irritation caused by environmental conditions or contact lenses, keratoconjunctivitis sicca, Sjögren's syndrome bacterial infections on the surface of the eye or related anterior structures caused by bacteria sensitive to chitosan, comprising administering, in a subject in need thereof, a therapeutically effective amount of a composition as described herewith.

In a further aspect of the invention is provided a method for preventing and/or treating an arthritic disease including osteoarthritis, and psoriatic arthritis, comprising administering, in a subject in need thereof, a therapeutically effective amount of a composition as described herewith.

Mode of Administration

Compositions of this invention may be administered in any manner including, but not limited to, orally, parenterally, sublingually, transdermally, transmucosally, topically, intraocularly, or combinations thereof.

For ophthalmic applications, an appropriate mode of administration of the composition according to the invention is a topical administration for instance as artificial tears or intravitreal and subconjunctival administrations.

For therapeutic applications in the treatment of an arthritic disease, intra-articular injections constitute an appropriate mode of administration of the composition according to the invention.

According to a particular embodiment, the compositions of Examples may be packaged either in monodose units or in appropriate multidose preservative-free containers. For instance, for ophthalmic applications, the composition of Example may be topically administered by instillation in the eye in convenient drop form.

Combination

According to the invention, a composition according to the invention can be administered alone or in combination with a co-agent useful in the prevention and/or treatment of the disease to be treated.

For instance, for treatment of dry eye syndrome with blepharitis, a composition according to the invention comprising chitosan and glycerol may further be administered with an antibiotic, an anti-inflammatory agent, an anti-glaucoma product (prostaglandin, beta-adrenergic blocker) an anti-allergic product.

For instance, a composition according to the invention comprising chitosan and glycerol may further be administered with a gel-forming agent such as alginate or a pullulan.

The invention encompasses the administration of the composition comprising chitosan and glycerol according to the invention wherein said agents are administered to an individual prior to, simultaneously or sequentially with other therapeutic regimens or co-agents useful in the prevention and/or treatment of the disease of interest, in a therapeutically effective amount. The compositions comprising chitosan and glycerol according to the invention which are administered simultaneously with said co-agents can be administered in the same or different compositions and in the same or different routes of administration.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying figures. Such modifications are intended to fall within the scope of the appended claims.

The invention having been described, the following examples are presented by way of illustration, and not limitation.

EXAMPLES

Example 1: Production of a Composition Comprising Chitosan (0.5%) and Glycerol According to the Invention 0.500 g of chitosan from fungus origin having an average molecular weight of 173 kDa and a degree of acetylation of 35% (mol) is solubilized in 55 g of aqueous solution containing 0.194 g of lactic acid (90%), at room temperature under magnetic stirring. After complete solubilisation of chitosan, 0.625 g of glycerol 85% and 42.3 g of aqueous solution containing 1.4 g of sodium succinate are added to the chitosan solution to increase pH to about 6.5 and osmolality to approximately 300 mOsmol/kg. Water is added to a final volume of 100 g. The solution is then autoclaved at 121° C. during 15 min. The resulting aqueous solution contains 0.5% of chitosan, 0.175 (w/w) lactic acid 1.40% (w/w) sodium succinate, 0.531% (w/w) glycerol has a viscosity of 18 mPas·s, a pH of 6.5, and an osmolality of 304 mOsmol/kg.

Example 2: Production of a Composition Comprising Chitosan (0.5%) and Glycerol According to the Invention 0.500 g of chitosan from fungus origin having a molecular weight of 172 kDa and a degree of acetylation of 32 mol (%) is solubilized in 55 g of aqueous solution containing 0.2045 g of lactic acid (90%), at room temperature under magnetic stirring. After complete solubilisation of chitosan, 0.625 g of glycerol 85% and 42.3 g of aqueous solution containing 1.4 g of sodium succinate are added to the chitosan solution to increase pH to about 6.5 and osmolality to approximately 300 mOsmol/kg. Water is added to a final volume of 100 g. The solution is then autoclaved at 121° C. during 15 min. The rheological profile of the solution is studied before and after heat sterilization. The resulting aqueous solution contains 0.5% of chitosan, 0.184% (w/w) lactic acid, 1.40% (w/w) sodium succinate, 0.531% (w/w) glycerol, and has a viscosity of 20 mPas·s, a pH of 6.5, and an osmolality of 318 mOsmol/kg before heat sterilization. After autoclaving, the resulting solution is clear, viscous and has a viscosity of 18 mPas·s, a pH of 6.4, and an osmolality of 322 mOsmol/kg. As shown in FIG. 1, the rheological profile of a composition according to the invention comprising 0.5% chitosan before and after heat sterilization show that glycerol protects the formulation from enhanced decrease of the dynamic viscosity during heat sterilisation.

Example 3: Production of a Composition Comprising Chitosan (0.4%), Glycerol, and a Pullulan, According to the Invention 1.00 g of pullulan (10 kDa) is solubilized in 55 g of aqueous solution containing 0.194 g of lactic acid (90%), at room temperature under magnetic stirring. After complete dissolution of pullulan, 0.400 g of chitosan from fungus origin having an average molecular weight of 159 kDa and a degree of acetylation of 31 mol (%) is solubilized. After complete solubilisation of chitosan, 0.625 g of glycerol 85% and 42.3 g of aqueous solution containing 1.4 g of sodium succinate are added to the chitosan solution to increase pH to about 6.5 and osmolality to approximately 300 mOsmol/kg. Water is added to a final volume of 100 g. The solution is then autoclaved at 121° C. during 15 min. The resulting aqueous solution contains 0.4% of chitosan, 1.0% of pullulan, 0.175% (w/w) lactic acid, 1.40% (w/w) sodium succinate, 0.531% (w/w) has a viscosity of 44 mPas·s, a pH of 6.5, and an osmolality of 320 mOsmol/kg.

Example 4: Production of a Composition Comprising Chitosan (0.3%), Glycerol, and a Pullulan, According to the Invention 1.00 g of pullulan is solubilized in 55 g of aqueous solution containing 0.194 g of lactic acid (90%), at room temperature under magnetic stirring. After complete dissolution of pullulan, 0.300 g of chitosan from fungus origin having a molecular weight of 159 kDa and a degree of acetylation of 31 mol (%) is solubilized. After complete solubilisation of chitosan, 0.625 g of glycerol 85% and 42.3 g of aqueous solution containing 1.4 g of sodium succinate are added to the chitosan solution to increase pH to about 6.5 and osmolality to approximately 300 mOsmol/kg. Water is added to a final volume of 100 g. The solution is then autoclaved at 121° C. during 15 min. The resulting aqueous solution contains 0.3% of chitosan, 1.0% of pullulan, 0.175% (w/w) lactic acid, 1.40% (w/w) sodium succinate, 0.531% (w/w) has a viscosity of 27 mPas·s, a pH of 6.6, and an osmolality of 318 mOsmol/kg.

Example 5: Production of a Composition Comprising Chitosan (0.4%), Glycerol, and a Pullulan, According to the Invention 0.50 g of pullulan (10 kDa) is solubilized in 55 g of aqueous solution containing 0.194 g of lactic acid (90%), at room temperature under magnetic stirring. After complete dissolution of pullulan, 0.400 g of chitosan from fungus origin having an average molecular weight of 159 kDa and a degree of acetylation of 31 mol (%) is solubilized. After complete solubilisation of chitosan, 0.625 g of glycerol 85% and 42.3 g of aqueous solution containing 1.4 g of sodium succinate are added to the chitosan solution to increase pH to about 6.5 and osmolality to approximately 300 mOsmol/kg. Water is added to a final volume of 100 g. The solution is then autoclaved at 121° C. during 15 min. The resulting aqueous solution contains 0.4% of chitosan, 0.5% of pullulan, 0.175% (w/w) lactic acid, 1.40% (w/w) sodium succinate, 0.531% (w/w) has a viscosity of 33 mPas·s, a pH of 6.5, and an osmolality of 325 mOsmol/kg.

Figure 2:
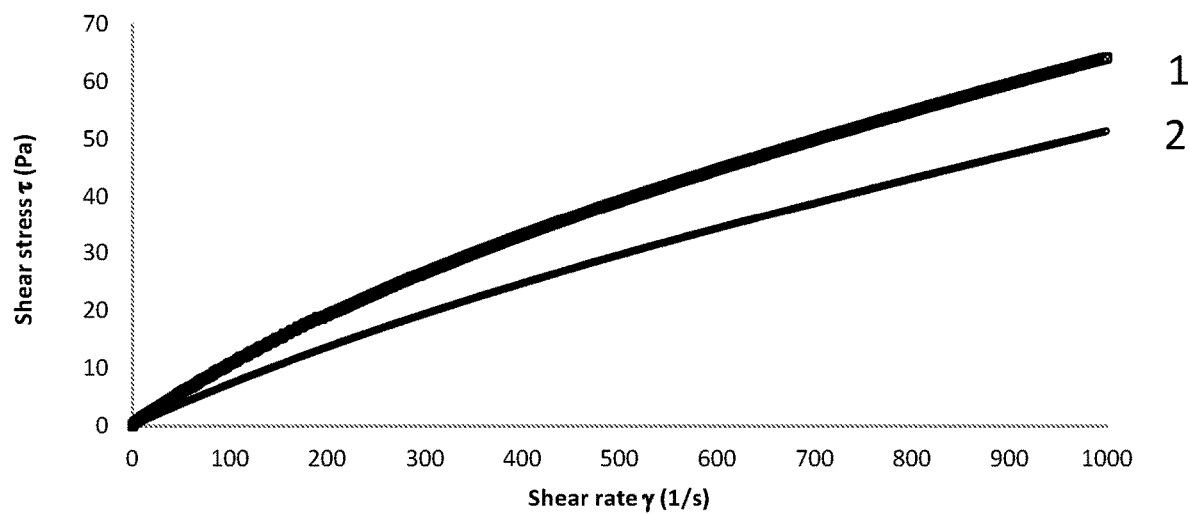
FIG. 2: rheological profile of the composition comprising 1% chitosan and glycerol according to Example 6 before (1) and after (2) heat sterilization.

Example 6: Production of a Composition Comprising Chitosan (1%) and Glycerol According to the Invention 1.0 g of chitosan from fungus origin having an average molecular weight of 159 kDa and a degree of acetylation of 31 mol (%) is solubilized in 55 g of aqueous solution containing 0.414 g of lactic acid (90%), at room temperature under magnetic stirring (dissolution time 5 h-9 h). After complete solubilisation of chitosan, 0.625 g of glycerol 85% and 42.3 g of aqueous solution containing 1.4 g of sodium succinate are added to the chitosan solution to increase pH to about 6.5 and osmolality to approximately 300 mOsmol/kg. Water is added to a final volume of 100 g. The solution is then autoclaved at 121° C. during 15 min. The resulting aqueous solution contains 1.0% of chitosan, 0.372% (w/w) lactic acid, 1.40% (w/w) sodium succinate, 0.531% (w/w) glycerol, has a viscosity of 73 mPas·s, a pH of 6.4, and an osmolality of 307 mOsmol/kg. As shown in FIG. 2, the rheological profile of a composition according to the invention comprising 1% chitosan before and after heat sterilization show that the glycerol protects the chitosan from enhanced decrease of the viscosity of the formulation during heat sterilization.

Figure 4:
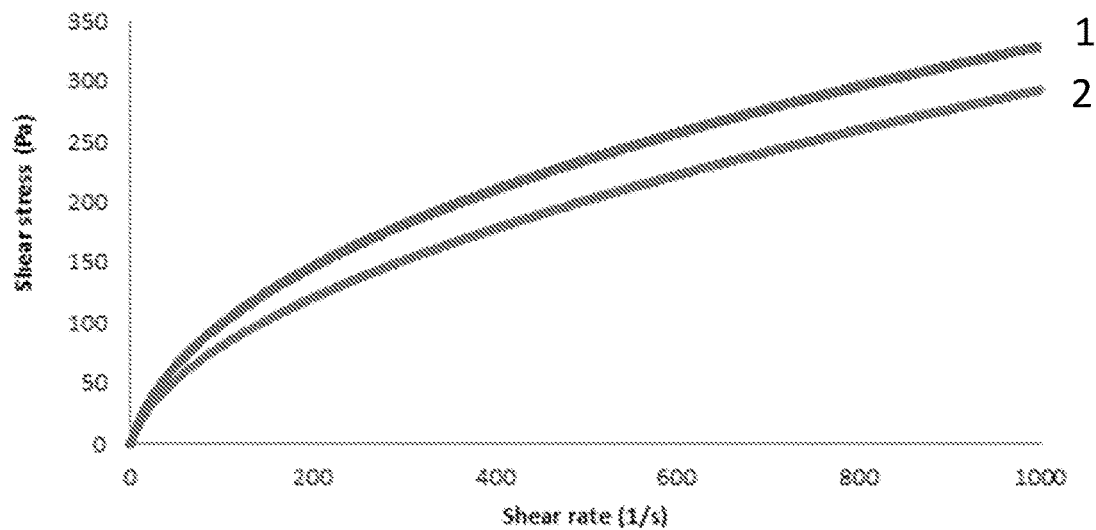
FIG. 4: rheological profile of the composition comprising 2% chitosan and glycerol according to Example 7 before (1) and after (2) heat sterilization.

Example 7: Production of a Composition Comprising Chitosan (2%) and Glycerol According to the Invention 2.0 g of chitosan from fungus origin having an average molecular weight of 159 kDa and a degree of acetylation of 31 mol (%) is solubilized in 55 g of aqueous solution containing 0.828 g of lactic acid (90%), at room temperature under magnetic stirring (dissolution time 5 h-9 h). After complete solubilisation of chitosan, 0.625 g of glycerol 85% and 42.3 g of aqueous solution containing 1.4 g of sodium succinate are added to the chitosan solution to increase pH to about 6.5 and osmolality to approximately 300 mOsmol/kg. Water is added to a final volume of 100 g. The solution is then autoclaved at 121° C. during 15 min. The resulting aqueous solution contains 2.0% of chitosan, 0.744% (w/w) lactic acid, 1.40% (w/w) sodium succinate, 0.531% (w/w) glycerol, has a viscosity of 802 mPas·s, a pH of 6.1, and an osmolality of 310 mOsmol/kg. As shown in FIG. 4, the rheological profile of a composition according to the invention comprising 2% chitosan before and after heat sterilization show that the glycerol protects the chitosan from enhanced decrease of the viscosity of the formulation during heat sterilization.

Example 8: Mucoadhesive Properties

Figure 3:
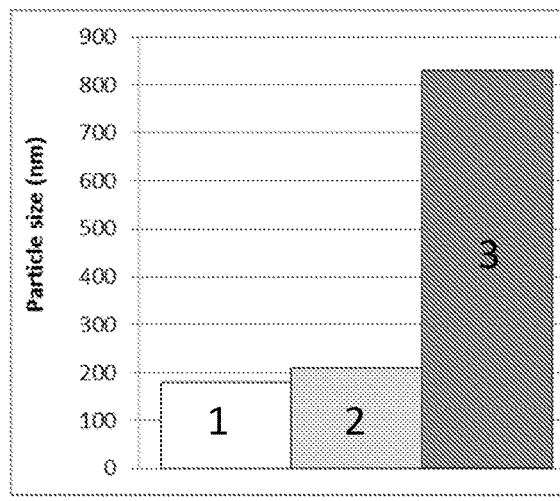
FIG. 3: Mucoadhesive properties of a composition of the invention based on particle size (A) and turbidity measurements (B) as described in Example 8, comparing a formulation of the invention comprising 0.5% chitosan and glycerol according to Example 2 in presence of mucin (3) with a hyaluronic acid solution in presence of mucin (2) and a mucin solution (1).
Figure 3:
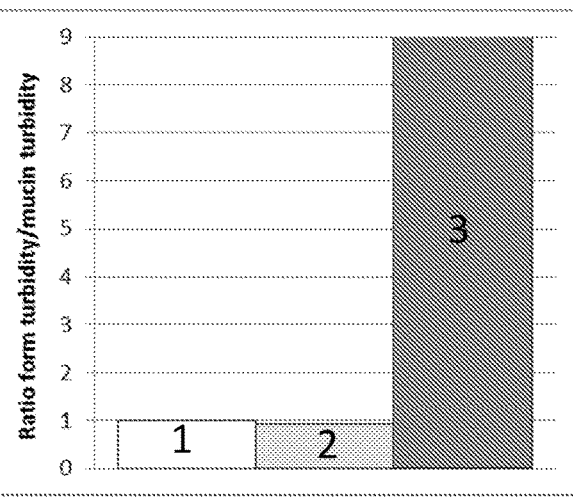

The mucoadhesive properties were evaluated in vitro using two methods, the particle size test and turbidity test and were compared to a standard 0.18% hyaluronic acid eye drop solution. The particle size test pointed out the formation of aggregates of 1 μm in size between chitosan from fungus origin and mucin, indicating mucoadhesion, whereas no aggregates were formed between mucin and hyaluronic acid. The same result was obtained using the turbidity test that showed an important increase in turbidity solution when the chitosan formulation was mixed with mucin, whereas no sign of increase in turbidity signal was observed when hyaluronic acid was mixed with mucin (FIG. 3).

Example 9: Anti-Lipase Activity

The anti-lipase activity was performed using the Lipase Activity Assay Kit II from BioVision. The lipase substrate is added to the composition containing chitosan (0.5%) and glycerol (0.625%) in the presence of a probe (DTNB) that changes the color from colorless to yellow depending on the activity of the lipase. In the presence of the composition comprising chitosan from fungus origin and glycerol, the probe remains colorless or slightly yellowish indicating that the composition according to the invention has an anti-lipase activity. The anti-lipase activity of composition of the invention may be a further advantage for uses of the invention.

Figure 5:
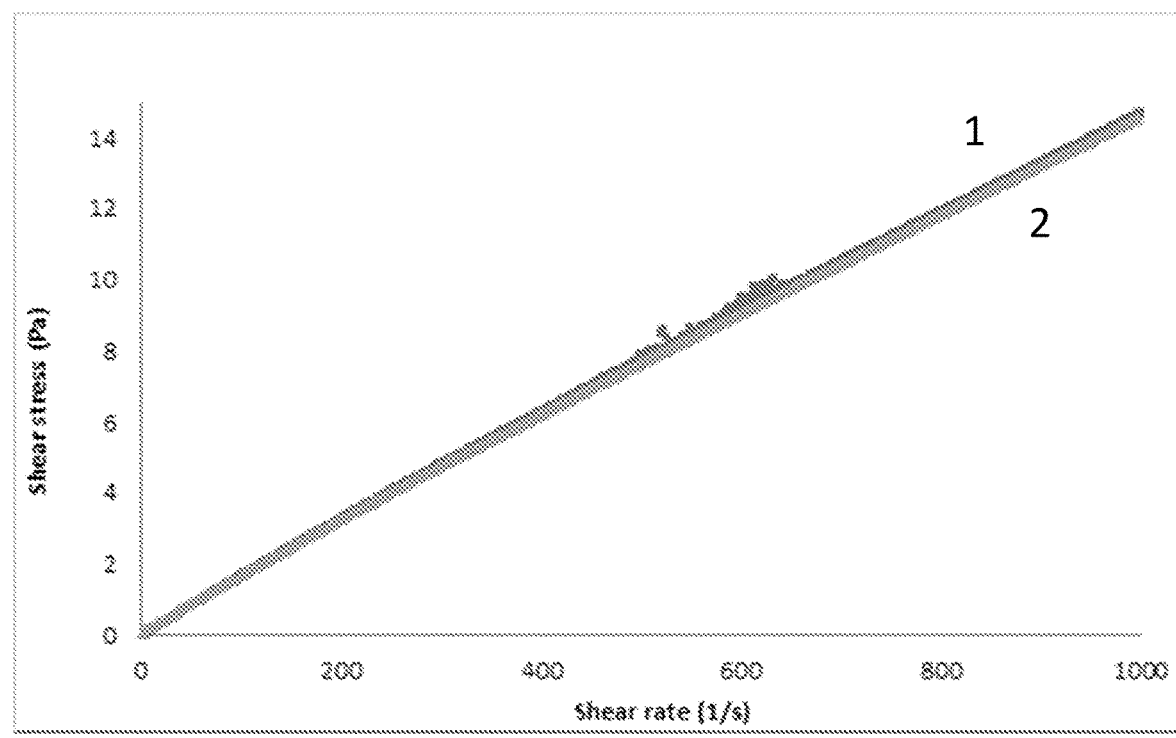
FIG. 5: rheological profile of the composition comprising 2% chitosan and glycerol according to Example 10 before (1) and after (2) heat sterilization.

Example 10: Production of a Composition Comprising Chitosan (0.5%) and Glycerol According to the Invention 0.500 g of chitosan of animal origin (Heppe Medical Chitosan, Deutschland) having an average molecular weight between 100-250 kDa and a degree of acetylation of 28 mol (%) is solubilized in 55 g of aqueous solution containing 0.219 g of lactic acid (90%), at room temperature under magnetic stirring. After complete solubilisation of chitosan, 0.625 g of glycerol 85% and 42.3 g of aqueous solution containing 1.4 g of sodium succinate are added to the chitosan solution to increase pH to about 6.5 and osmolality to approximately 300 mOsmol/kg. Water is added to a final volume of 100 g. The solution is then autoclaved at 121° C. during 15 min. The rheological profile of the solution is studied before and after heat sterilization. The resulting aqueous solution contains 0.5% of chitosan, 0.197% (w/w) lactic acid, 1.40% (w/w) sodium succinate, 0.531% (w/w)

glycerol, and has a viscosity of 18 mPas·s, a pH of 6.5, and an osmolality of 318 mOsmol/kg before heat sterilization. After autoclaving, the resulting solution is clear, viscous and has a viscosity of 17 mPas·s, a pH of 6.5, and an osmolality of 315 mOsmol/kg. As shown in FIG. 5, the rheological profile of a composition according to the invention comprising 0.5% chitosan before and after heat sterilization show that glycerol protects the formulation from enhanced decrease of the dynamic viscosity during heat sterilization.

Example 11: Production of a Composition Comprising Chitosan (0.5%) According to a Process of the Invention as Compared to Other Processes Formulation containing 0.5% of chitosan from fungus origin were prepared using different processes, namely: comparison process a) all excipients (lactic acid, Na succinate, glycerol) were mixed, the resulted solution was sterilised by heat-sterilisation and thereafter chitosan was added; process of the invention b) chitosan was solubilised in lactic acid; Na succinate and glycerol were then added and the final solution was sterilised by heat-sterilisation; comparison process c) chitosan was added to Na succinate and glycerol solution, the resulted suspension was sterilised by heat-sterilisation and thereafter lactic acid was added to solubilise chitosan. The pH, osmolality were measured and the results are shown in Table 1.

TABLE 1

|  | Appearance of final solution | pH | Osmolality (mOsmol/kg) |
|---|---|---|---|
| Process a | large aggregates | 6.5 | 349 |
| Process b | Clear, without visible particles | 6.5 | 298 |
| Process c | large aggregates | 6.5 | 326 |

The above results show that only process of the invention b is leading to a final formulation without visible particles and therefore is suitable for the preparation of composition for ophthalmic use.

Example 12: Compositions Comprising Chitosan (1%) According to the Invention as Compared to Comparison Formulations Several formulations with two different percentages of chitosan were solubilized in different acids as indicated in Table 2. Sufficient volume of acid was added to completely solubilize chitosan from fungus origin. Thereafter, various bases were added to increase the pH to 6.5. The turbidity as well as the osmolarity of each solution were evaluated. The results are shown in Table 2.

TABLE 2

| Chitosan percentage (%) | Acid | Base | Turbidity | Osmolarity (mOsmol/kg) |
|---|---|---|---|---|
| EX 8 | 1.0 | Lactic acid | Sodium Lactate | low | 786 |
| EX 9 | 1.0 | Lactic acid | Potassium Gluconate | low | 402 |
| EX 10 | 1.0 | Lactic acid | Sodium Succinate | low | 147 |
| EX 11 | 1.0 | Lactic acid | Potassium Sorbate | low | 246 |

TABLE 2-continued

| Chitosan percentage (%) | Acid | Base | Turbidity | Osmolarity (mOsmol/kg) |
|---|---|---|---|---|
| COMP 1 | 1.0 | Lactic acid | NaOH | high | 148 |
| COMP 2 | 1.0 | Lactic acid | NaOH | high | 172 |
| EX 12 | 1.0 | Galactic acid | Sodium Lactate | low | 1223 |
| EX 13 | 1.0 | Galactic acid | Potassium Gluconate | low | 1588 |
| EX 14 | 1.0 | Galactic acid | Sodium Succinate | low | 1102 |
| COMP 3 | 0.5 | HCl (1M) | NaOH | Precipitation | ND |
| COMP 4 | 0.5 | HCl (1M) | Succinate | high | 311 |

Those data support the fact that the use of a weak acid and a weak base are necessary in the process of the invention since strong acid or base were not suitable since the solution was too turbid (COMP 1-4). Further, the osmolarity results showed that lactic acid (weak acid) and succinate or sorbate (weak bases) are particularly suitable for the preparation of an ophthalmic solution since they allow reaching a target osmolarity of 300 mOsmol/kg, suitable for an ophthalmic application.

The invention claimed is:

1. A process for preparing a heat-sterilized aqueous composition comprising solubilized chitosan and glycerol, wherein said composition is a clear and viscous solution, at a pH between 6 and 7.5, wherein said process comprises the following steps:
   (i) solubilizing chitosan having an average molecular weight ranging from about 10 kDa to about 250 kDa and a degree of deacetylation higher than 60% in an aqueous solution of a weak acid comprising a carboxylic group, wherein the molar ratio between the carboxyl group (—COOH) of said weak acid and the amine group (—NH$_2$) of said chitosan is between 1:0.9 and 1:1.1;
   (ii) adding glycerol;
   (iii) adjusting the pH to a pH between 6 and 7.5 by addition of an aqueous solution of weak base; and
   (iv) steam sterilizing;
   thereby forming a heat-sterilized composition comprising solubilized chitosan and glycerol that is a clear and viscous solution at a pH between 6 and 7.5.

2. The process according to claim 1, wherein said weak acid is lactic acid.

3. The process according to claim 1, wherein the weak base is selected from sodium succinate and potassium sorbate.

4. The process according to claim 1, wherein:
   in step (i), said chitosan is present at a concentration between 0.05 and 3% (w/w), and said weak acid is lactic acid present at a concentration between 0.12 and 0.22% (w/w),
   in step (ii), said glycerol is present at a concentration between 0.4 and 1% (w/w), and
   in step (iii), said weak base is sodium succinate present at a concentration between 1.0 and 1.7% (w/w).

5. The process according to claim 1, wherein said chitosan of step (i) has an average Molecular Weight (MW) ranging from about 150 to about 180 kDa and a degree of deacetylation (DD) between 60% (mol) and 75% (mol).

6. The process according to claim 1, wherein said chitosan of step (i) is a chitosan of fungal origin.

7. The process according to claim 1, wherein the chitosan is solubilized under step (i) in an aqueous solution of weak acid further comprising a solubilized pullulan.

8. The process according to claim 1, wherein the molar ratio between the carboxyl group (—COOH) of said weak acid and the amine group (—$NH_2$) of said chitosan is between 1:1 or 1:1.05.

* * * * *